United States Patent
Lovett et al.

(10) Patent No.: US 7,308,319 B2
(45) Date of Patent: Dec. 11, 2007

(54) DELIVERY SYSTEM AND METHOD USING PULMONARY ARTERY FOR PLACEMENT OF RV LEADS

(75) Inventors: Eric G. Lovett, Mendota Heights, MN (US); Bruce A. Tockman, Scandia, MN (US); Yongxing Zhang, Maple Grove, MN (US); Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 141 days.

(21) Appl. No.: 10/970,569

(22) Filed: Oct. 21, 2004

(65) Prior Publication Data

US 2006/0089693 A1  Apr. 27, 2006

(51) Int. Cl.
*A61N 1/05* (2006.01)
(52) U.S. Cl. ........................ 607/119; 128/898
(58) Field of Classification Search ................ 607/119
See application file for complete search history.

(56) References Cited

U.S. PATENT DOCUMENTS

| | | | |
|---|---|---|---|
| 3,995,623 A | 12/1976 | Blake et al. |
| 4,024,873 A | 5/1977 | Antoshkiw et al. |
| 4,402,328 A | 9/1983 | Doring |
| 4,488,561 A | 12/1984 | Doring |
| 4,595,009 A | 6/1986 | Leinders |
| 4,627,439 A | 12/1986 | Harris |
| 4,641,656 A | 2/1987 | Smits |
| 4,643,201 A | 2/1987 | Stokes |
| 4,651,751 A | 3/1987 | Swendson et al. |
| 4,986,270 A | 1/1991 | Cohen |
| 5,016,808 A | 5/1991 | Heil, Jr. et al. |
| 5,029,585 A | 7/1991 | Lieber et al. |
| 5,144,960 A | 9/1992 | Mehra et al. |
| 5,314,462 A | 5/1994 | Heil et al. |
| 5,387,233 A | 2/1995 | Alferness et al. |
| 5,403,351 A | 4/1995 | Saksena |
| 5,405,374 A | 4/1995 | Stein |
| 5,411,527 A | 5/1995 | Alt |
| 5,423,772 A | 6/1995 | Lurie et al. |
| 5,423,865 A | 6/1995 | Bowald et al. |

(Continued)

OTHER PUBLICATIONS

Giudici, M.C., "Improvement in Cardiac Output with Right Ventricular Outflow Septal Pacing Compare to Apical Pacing is Independent of Pre-existing Conduction Disease", *Pacing and clinical electrophusiology: PACE*, 23(4). (2000), 748.

(Continued)

*Primary Examiner*—Carl Layno
*Assistant Examiner*—Christopher A. Flory
(74) *Attorney, Agent, or Firm*—Faegre & Benson LLP

(57) ABSTRACT

A delivery system and method for delivering a right ventricular lead into a right ventricle includes a delivery device having an inflatable balloon at a distal end. The device is inserted into the venous system, the balloon is inflated and the device is floated along a blood flow path within the venous system through the heart and into the pulmonary artery. The lead is delivered into the right ventricle using the device. In one embodiment, the device is a catheter that facilitates placement of a guide wire into the right ventricle for delivery of the lead. The catheter is then removed and the lead is inserted into the right ventricle over the guide wire.

7 Claims, 6 Drawing Sheets

U.S. PATENT DOCUMENTS

| | | | |
|---|---|---|---|
| 5,433,729 | A | 7/1995 | Adams et al. |
| 5,487,727 | A | 1/1996 | Snider et al. |
| 5,571,159 | A | 11/1996 | Alt |
| 5,609,621 | A | 3/1997 | Bonner |
| 5,628,779 | A | 5/1997 | Bornzin et al. |
| 5,643,338 | A | 7/1997 | Bornzin et al. |
| 5,697,965 | A | 12/1997 | Griffin, III |
| 5,788,647 | A | 8/1998 | Eggers |
| 5,861,023 | A | 1/1999 | Vachon |
| 5,922,014 | A | 7/1999 | Warman et al. |
| 5,925,073 | A | 7/1999 | Chastain et al. |
| 6,006,122 | A | 12/1999 | Smits |
| 6,021,354 | A | 2/2000 | Warman et al. |
| 6,076,014 | A | 6/2000 | Alt |
| 6,093,982 | A | 7/2000 | Kroll |
| 6,117,128 | A | 9/2000 | Gregory |
| 6,132,390 | A | 10/2000 | Cookston et al. |
| 6,245,064 | B1 | 6/2001 | Lesh et al. |
| 6,363,286 | B1 | 3/2002 | Zhu et al. |
| 6,363,287 | B1 | 3/2002 | Brabec et al. |
| 6,454,721 | B1 | 9/2002 | deBoisblanc et al. |
| 6,501,992 | B1 | 12/2002 | Belden et al. |
| 6,532,378 | B2 | 3/2003 | Saksena et al. |
| 6,579,259 | B2 | 6/2003 | Stevens et al. |
| 6,666,826 | B2 | 12/2003 | Salo et al. |
| 6,718,211 | B2 | 4/2004 | Smits |
| 6,760,619 | B1 | 7/2004 | Helland et al. |
| 6,882,886 | B1 | 4/2005 | Witte et al. |
| 2004/0122496 | A1 | 6/2004 | Zhang et al. |
| 2004/0122497 | A1 | 6/2004 | Zhang et al. |
| 2004/0122498 | A1 | 6/2004 | Zhang et al. |
| 2004/0215139 | A1* | 10/2004 | Cohen ............... 604/95.04 |
| 2004/0260374 | A1 | 12/2004 | Zhang et al. |
| 2004/0260375 | A1 | 12/2004 | Zhang et al. |
| 2005/0149155 | A1 | 7/2005 | Scheiner et al. |
| 2005/0149156 | A1 | 7/2005 | Libbus et al. |
| 2006/0173298 | A1* | 8/2006 | Tucker ............... 600/433 |

OTHER PUBLICATIONS

Libbus, Imad, "Lead for Stimulating the Baroreceptors in the Pulmonary Artery", U.S. Appl. No. 10/746,861, filed Dec. 24, 2003, 21 pages.

Scheiner, Avram, "Stimulation Lead for Stimulating the Baroreceptors in the Pulmonary Artery", U.S. Appl. No. 10/746,852, filed Dec. 24, 2003, 25 pages.

Scherlag, B. J., et al., "Endovascular stimulation within the left pulmonary artery to induce slowing of heart rate and paroxysmal atrial fibrillation.", *Cardiovasc Reasearch*, 54(2). (May 2002), 470-475.

Tse, Hung-Fat, "functional abnormalities in patients with permanent right venticular pacing—The effect of sites of electrical stimulation", *Journal of the American College of Cardiology*, 40(8). (Oct. 16, 2002), 1451-1458.

Barin, E. S., et al., "The Right Ventricular Outflow Tract as an Alternative Permanent Pacing Site: Long-term Follow-up", *Pacing and Clinical Electrophysiogy*, 14(1), (1991), 3-6.

Belham, M, et al., "Pacing Different Ventricular Sites with Active and Passive Fixation Leads: Comparison of Pacing Energy Requirements", *Pacing and Clinical Electrophysiogy*, 21(II), (1999), 977.

Buckingham, T. A., et al., "Right Ventricular Outflow Tract Pacing", *Pacing and Electrophysiology*, 20 (5 Pt. 1), (1997), 1237-42.

Giudici, M., et al., "Comparison of Right Ventricular Outflow Tract and Apical Lead Permanent Pacing on Cardiac Output", *American Journal of Cardiology*, 79(2), (1997), 209-212.

Giudici, M. C., et al., "Right Ventricular Outflow Tract Pacing Improves Haemodynamics in Patients with Class III-IV Heart Failure and Existing Apical Leads", *Pacing and Electrophysiology*, 21 (II) Abstract 751, (1998), 2 pgs.

Harris, Z. I., et al., "Changes in Left Ventricular Function and Dimensions Between Apical and Septal Lead Position with Dual Chamber Pacing in Normally Functioning Hearts", *Pacing and Clinical Electrophysiology*, 22(II) Abstract, (1999), 751.

Harris, Z. I., et al., "Septal/Right Ventricular Outflow Tract (RVOT) Lead Placement", Letters to the Editor, *Pacing and Electrophysiology*, 22(12), (1999), 1854.

Hirschberg, J., "A New Dual Chamber Single Lead System", *Pacing and Electrophysiology*, 17 (11 Pt. 2), (Nov. 1994), 1870-1872.

Lubinski, A., et al., "Implantation and Follow-up of ICD Leads Implanted in the Right Ventricular Outflow Tract", *Pacing and Electrophysiology*, 23 (11 Pt. 2), (2000), 1996-98.

Mera, F., et al., "A Comparison of Ventricular Function During High Right Ventricular Septal and Apical Pacing After His-bundle Ablation for Refractory Atrial Fibrillation", *Pacing and Clinical Electrophysiology*, 22(8), (1999), 1234-39.

Rosenqvist, M., et al., "The Effect of Ventricular Activation Sequence on Cardiac Performance During Pacing", *Pacing and Electrophysiology*, 19(9), (1996), 1279-1286.

Schwaab, B., et al., "Influence of Right Ventricular Stimulation Site on Left Ventricular Function in Atrial Synchronous Ventricular Pacing", *Journal of the American College of Cardiology*, 33(2), (1999), 317-23.

Schwaab, B., et al., "Surface ECG Guided Right Ventricular Septal Lead Implantation for the Reduction of Paced QRS Duration", *Pacing and Clinical Electrophysiology*, 21(II) (1999), 806.

Stainiewicz, J., et al., "Short Versus Long Term Results in Right Ventricular Outflow Tract Pacing—Prospective Randomized Study", *Pacing and Electrophysiology*, 21(II) Abstract 419, (1998), 894 #419.

Swan Ganz Catheter, Ohio State University Medical Center, Department of Inpatient Nursing, Jun. 2002 (Brochure) 1 pg.

Tang, A. S. L., et al., "Nonthorocotomy Implantation of Cardioverter Defibrillators; Preliminary Experience with a Defibrillation Lead Paced at the Right Ventricular Outflow Tract", *Pacing and Electrophysiology*, 19(6), (1996), 960-964.

Tantengco, M. V., et al., "Left Ventricular Dysfunction After Long-term Right Ventricular Apical Pacing in the Young", *American Journal of Cardiology*, 37(8), (Jun. 15, 2001), 2093-100.

Victor, F., et al., "Optimal Right Ventricular Pacing Site in Chronically Implanted Patients", *Journal of the American College of Cardiology*, 33(2), (1999), 311-6.

Vlay, S. C., et al., "Alternative Locations for Internal Defibrillator Electrodes", *Pacing and Clinical Electrophysiology*, 21(6), (1998), 1309-12.

Wolfhard, U. F., et al., "Alternative Lead Positioning in the Right Ventricular Outflow Tract in Transvenous Implantation if ICDs", *Pacing and Electrophysiology*, 18(1 Pt. 2), (1995), 179-81.

Office Action received in related case U.S. Appl. No. 10/970,265; mailed Jun. 16, 2006.

Office Action received in related case U.S. Appl. No. 10/970,265; mailed Nov. 7, 2006.

* cited by examiner

DELIVERY SYSTEM AND METHOD USING PULMONARY ARTERY FOR PLACEMENT OF RV LEADS

CROSS REFERENCE TO RELATED APPLICATIONS

This application is related to co-pending and co-owned application entitled DELIVERY SYSTEM AND METHOD FOR PULMONARY ARTERY LEADS, filed on the same day and assigned Ser. No. 10/970,265, which is herein incorporated by reference.

TECHNICAL FIELD

The present invention is related to the field of medical leads and related delivery systems and, in particular, to a delivery system for RV leads utilizing the pulmonary artery.

BACKGROUND

Cardiac leads have been placed in various locations within the heart structure in order to provide access for monitoring heart function and providing electrical stimulus to affect heart rhythm. One area of placement for such cardiac leads is the right ventricle ("RV"). RV leads are often used with implantable cardiac devices, such as pacemakers or defilbrillators, depending on the type of heart failure or heart disease being experienced by the patient. The devices and are, at present, implanted by electrophysiologists who are highly specialized and trained in these techniques.

One barrier to conventional implantation of cardiac devices by general cardiologists or primary care physicians, that is by non-electrophysiologists, is the placement of the transvenous lead system. This placement commonly involves the use of a fluoroscope to monitor the progress of the device as it is guided through tortuous vasculature, into and through the heart chambers and into placement in specific locations within the heart or related vessels.

Now, in order to facilitate easy and fast implantation of RV leads, reduction in facility costs and reduction in exposure to radiation, there is a need for a delivery system and procedure for RV leads that allows for implantation by a non-specialized practitioner. Such implantation would ideally be accomplished without, or with minimal, use of a fluoroscope.

SUMMARY

The present invention is a delivery system and method for delivering a right ventricular lead into a right ventricle includes a delivery device having an inflatable balloon at a distal end. The device is inserted into the venous system, the balloon is inflated and the device is floated along a blood flow path within the venous system through the heart and into the pulmonary artery. The lead is delivered into the right ventricle using the device. In one embodiment, the device is a catheter that facilitates placement of a guide wire into the right ventricle for delivery of the lead. The catheter is then removed and the lead is inserted into the right ventricle over the guide wire.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
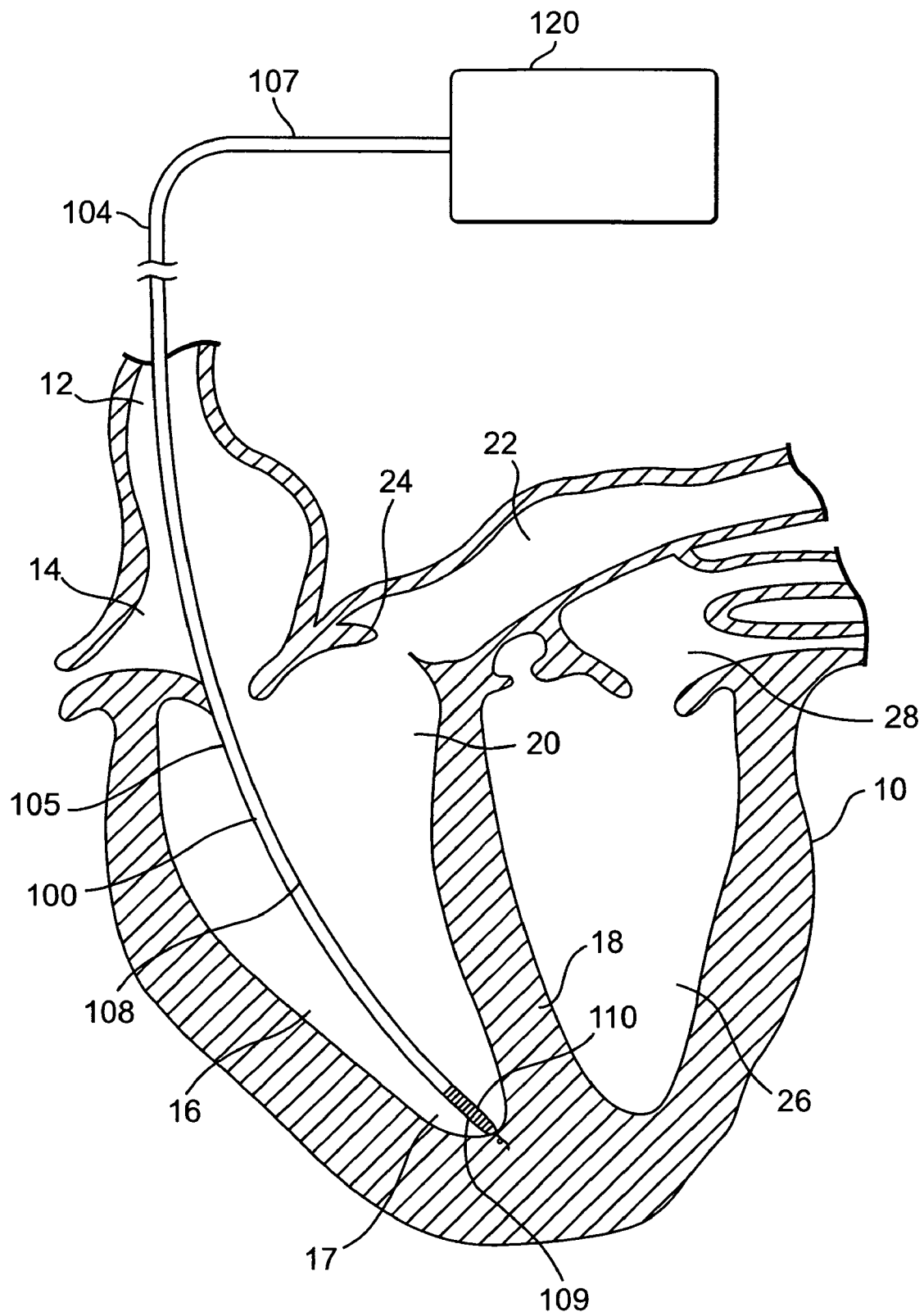
FIG. 1 shows a prior art right ventricular lead implanted into the right ventricle and connected to an implanted pulse generator.

FIG. 1 shows a view of a lead 100 implanted within a heart 10. The heart 10 generally includes a superior vena cava 12, a right atrium 14, a right ventricle 16, a ventricular septum 18, a ventricular outflow tract 20, which leads to a pulmonary artery 22 having a pulmonary artery valve 24, a left ventricle 26 and a left atrium 28. In one embodiment, the lead 100 is adapted to deliver defibrillation pulses to the heart 10 via an electrode 110 positioned in the right ventricle 16 near a ventricular apex 17. In this embodiment, the lead 100 is part of an implantable system including a pulse generator 120, such as a defibrillator or cardiac pacemaker.

The lead 100 includes a lead body 105 that extends from a proximal end 107 to a distal end 109 and has an intermediate portion 108. Lead 100 includes one or more conductors, such as coiled conductors, to conduct energy, such as from pulse generator 120 to heart 10, and also to receive signals from the heart 10. The lead 100 further includes outer insulation 104 to insulate the conductor. The conductors are coupled to one or more electrodes, such as electrode 110.

Figure 2:
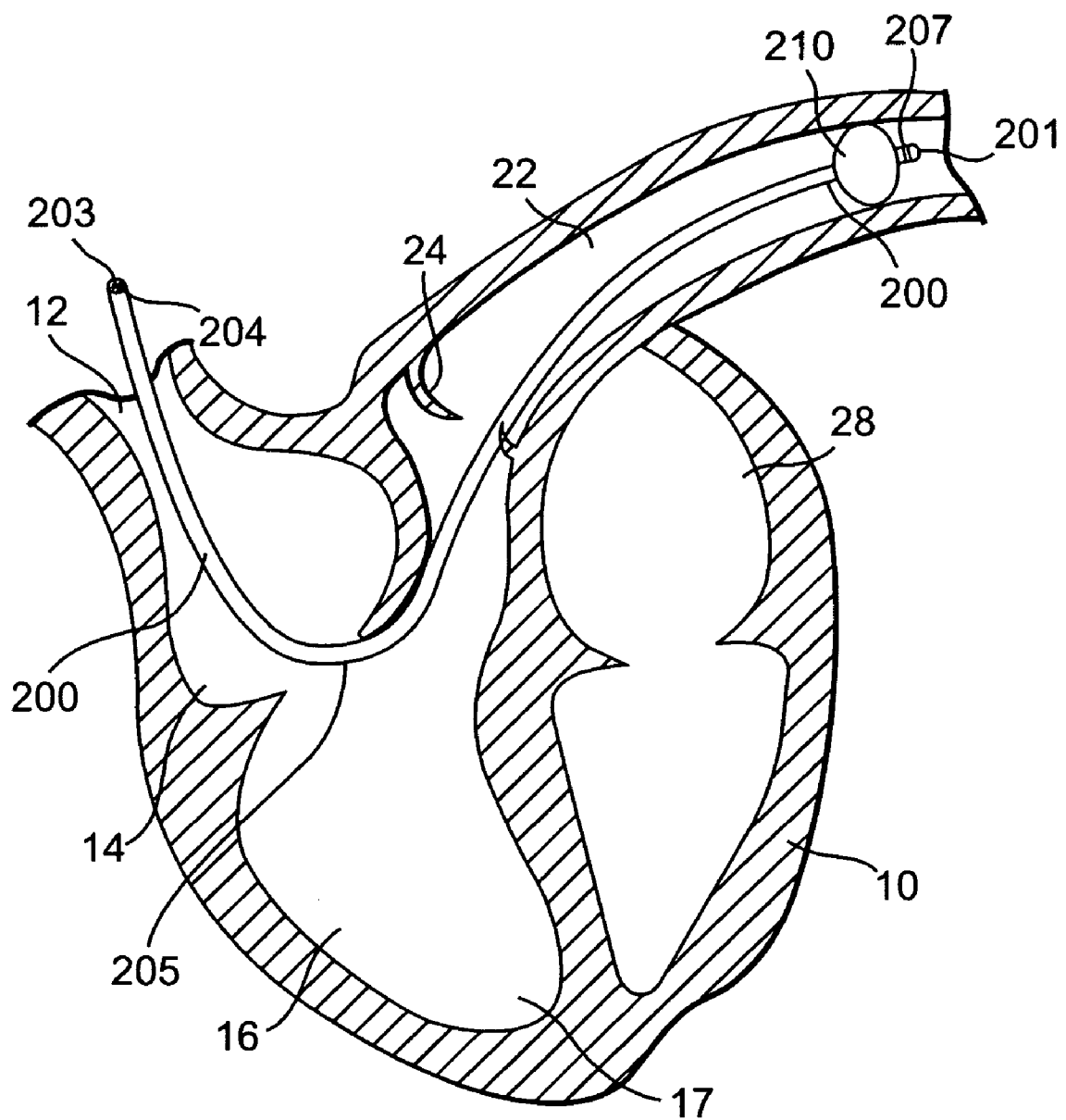
FIG. 2 shows a catheter having an inflatable balloon positioned within the pulmonary artery.

The present invention provides a delivery system for delivering an RV lead to the right ventricular apex 17 in an easy and efficient manner using a delivery device, such that even a non-specialized practitioner may perform the implantation. In FIG. 2, a first embodiment of the delivery system includes a catheter 200 having a flexible member 205 with an inflatable balloon 210 positioned at a distal end 201. The catheter 200 includes at least a guide wire lumen 203 and an inflation lumen 204. The guide wire lumen 203 may be centered or may be off center and extends from a proximal end to the distal end 201. The inflation lumen 204 may also extend from a proximal end to the balloon 210 or, alternatively, it may branch from the catheter 200 at a proximal end to facilitate easier inflation of the balloon 210.

In one embodiment, the catheter 200 is similar to the Swan Ganz catheters described in U.S. Pat. No. 3,995,623, which is herein incorporated by reference. The catheter 200 is placed within a vein in a conventional manner and the balloon 210 is then inflated allowing the balloon 210 and attached flexible catheter 200 to flow through the venous system into the heart 10 and out to the pulmonary artery 22. Further inflation of the balloon 210 affixes the catheter 200 temporarily within the pulmonary artery 22.

The catheter 200 is formed from a bio-compatible material, such as a flexible bio-compatible polymer, as is now known or later developed in the industry. In a similar manner, the balloon 210 is also formed from a bio-compatible material, such as thin, flexible latex or other suitable material. The catheter 200 may be sized as an 8 French or smaller.

A radiopaque marker 207 may optionally be provided on the distal end 201 of the catheter 200. This marker 207 may be used with a fluoroscopic or radiographic device to monitor the location of the catheter 200 within the venous system.

Figure 3:
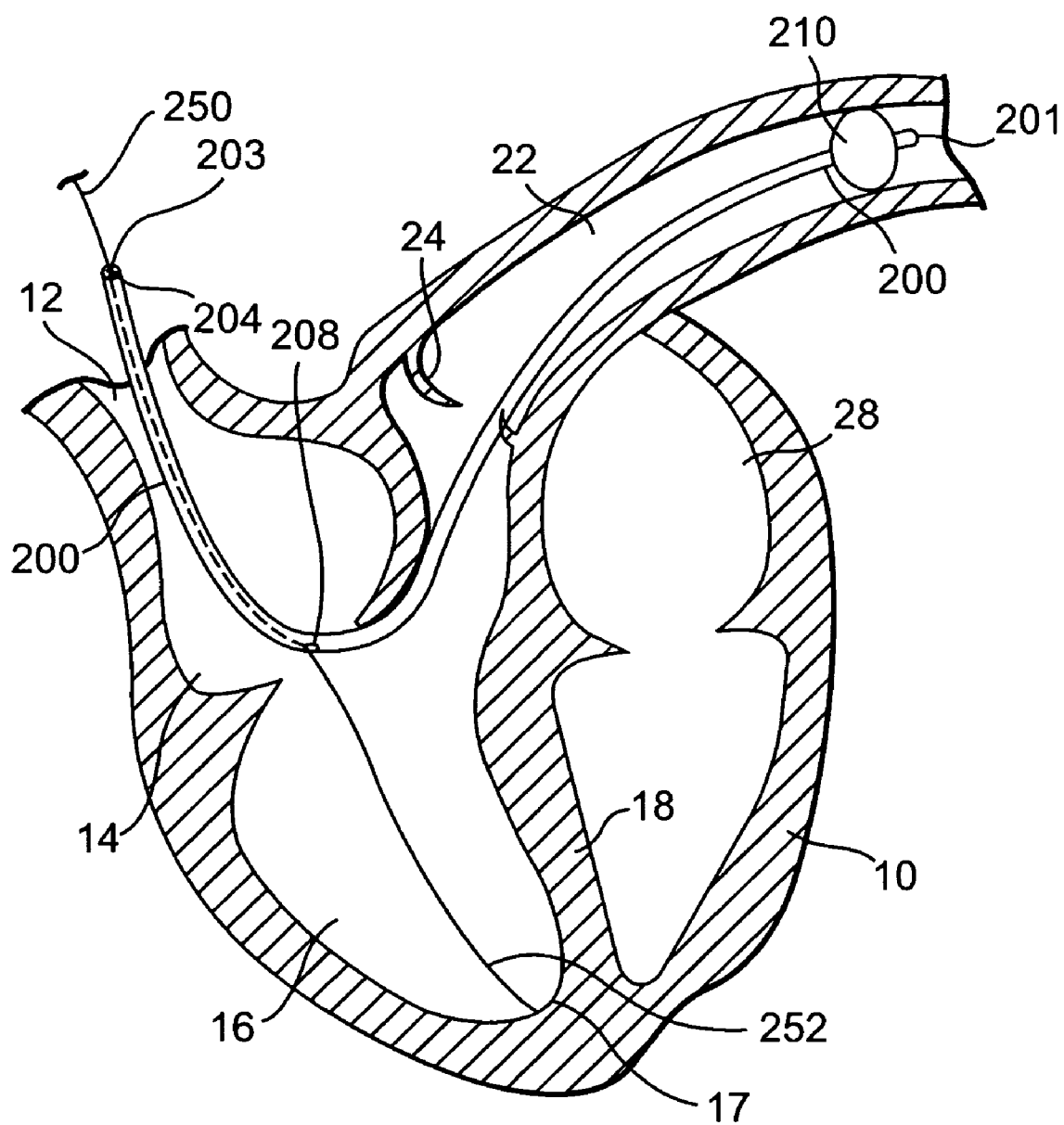
FIG. 3 shows a guide wire positioned into the right ventricular apex using the pulmonary artery catheter of FIG. 2.

Once the catheter 200 is located within the pulmonary artery 22, a guide wire 250 may be inserted into the guide wire lumen 203 of the catheter 200, as shown in FIG. 3. The guide wire 250 is then guided through an aperture 208 in the catheter 200 such that the guide wire 250 exits the catheter 200 in the right ventricle 16. The guide wire 250 is positioned with a distal end 252 in the right ventricular apex 17.

Figure 4:
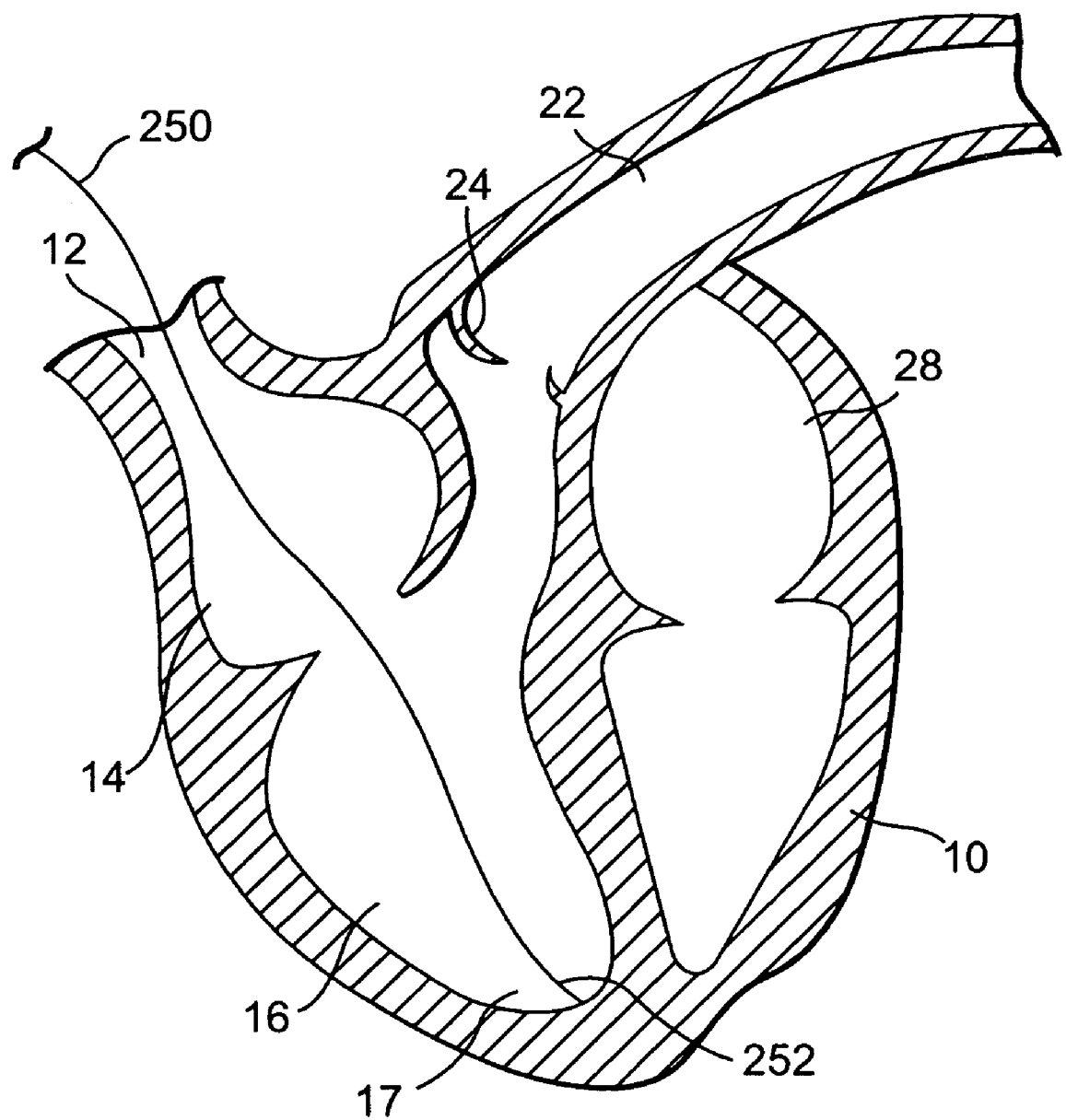
FIG. 4 shows the guide wire of FIG. 3 after the catheter has been removed.

When the guide wire 220 is in place, the catheter 200 may be removed, as shown in FIG. 4.

Figure 5:
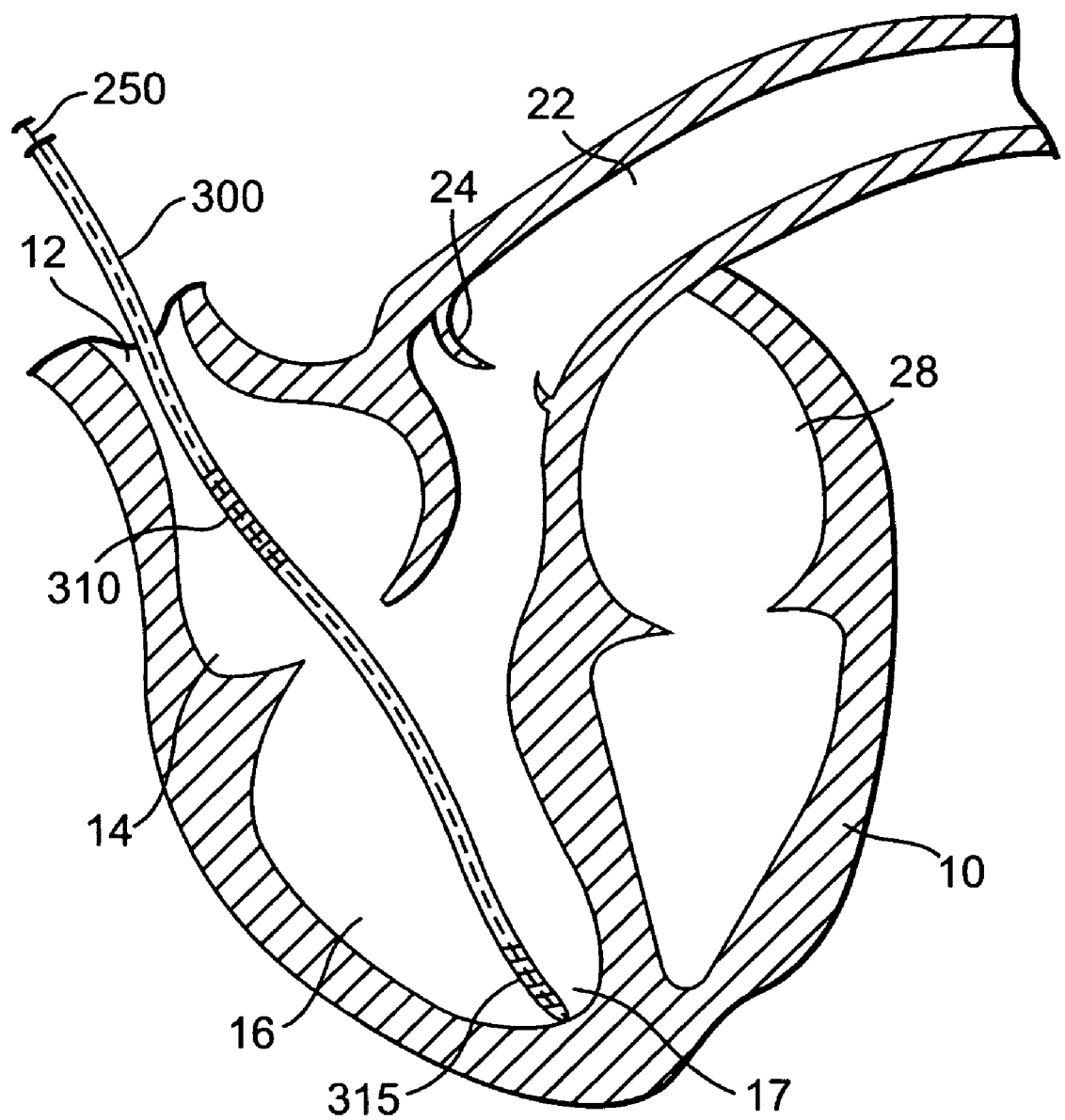
FIG. 5 shows a right ventricular lead positioned in the right ventricle using the guide wire of FIG. 4.

In FIG. 5, an RV lead 300 is shown positioned into the right ventricle 16 at or near the right ventricular apex 17. The RV lead 300 is guided into the appropriate position using the guide wire 250, as is known in the art. The RV lead 300 includes one or more electrodes 310, 315 positioned as needed for use in the intended cardiac electrical therapy.

Figure 6:
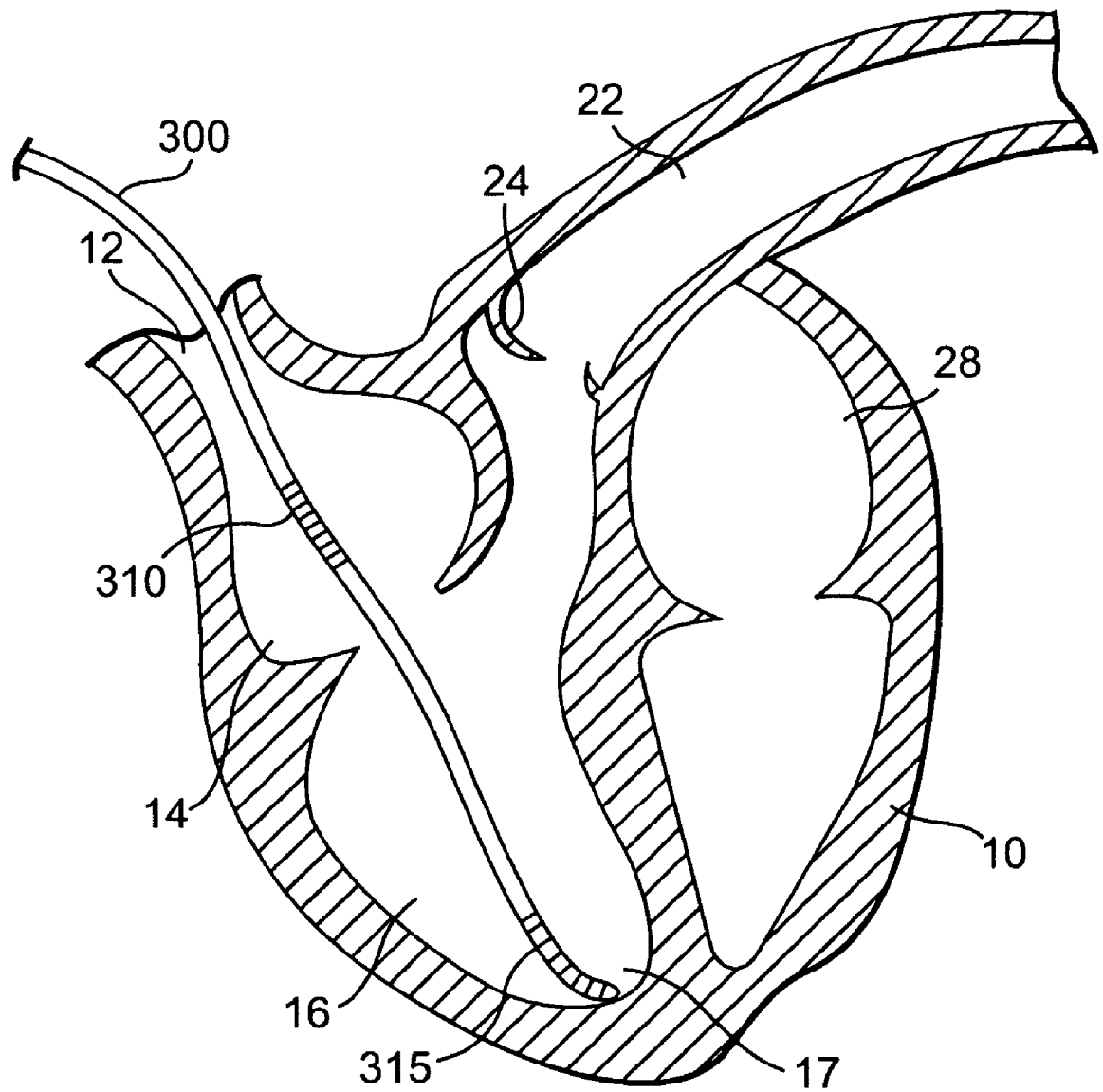
FIG. 6 shows the right ventricular lead of FIG. 5 after the guide wire has been removed.

When the RV lead 300 is in place, the guide wire 250 may be removed, as shown in FIG. 6. The RV lead 300 is then fixed in the right ventricle 16 in an appropriate manner.

Alternatively, an implantation catheter or other suitable intermediary device, which is now known or later developed in the industry, may be positioned into the right ventricle 16 using the guide wire 250. This intermediary device may then be used to insert the RV lead 300 in an appropriate manner.

Although the present invention has been described with reference to exemplary embodiments, persons skilled in the art will recognize that changes may be made in form and detail without departing from the spirit and scope of the invention.

We claim:

1. A method of delivering a cardiac lead into a right ventricle, the method comprising the steps of:
    inserting a distal end of a catheter into a venous system, the catheter including an inflatable balloon positioned near the distal end;
    inflating the balloon such that the balloon and catheter are carried along a blood flow path into a pulmonary artery;
    inserting a guide wire through the catheter into the right ventricle; and
    removing the catheter from the pulmonary artery before delivering a cardiac lead over the guide wire into the right ventricle.

2. The method of claim 1 further comprising the step of fixing the right ventricular lead within the right ventricle.

3. The method of claim 1 wherein the step of delivering includes positioning the right ventricular lead into a right ventricular apex.

4. The method of claim 1 wherein the catheter comprises an aperture and wherein the aperture is positioned within the right ventricle when the catheter is carried by the blood flow path into the pulmonary artery.

5. The method of claim 4 wherein the step of inserting the guide wire includes directing the guide wire out of the catheter through the aperture.

6. The method of claim 4 wherein the catheter is oriented so that the guide wire is released in the direction of a right ventricular apex.

7. The method of claim 1 wherein the catheter further comprises a radiopaque marker and further comprising the step of monitoring the location of the catheter by fluoroscopic monitoring of the radiopaque marker.

* * * * *